United States Patent [19]
Sapsford et al.

[11] Patent Number: 6,153,173
[45] Date of Patent: Nov. 28, 2000

[54] PROPELLANT MIXTURE FOR AEROSOL FORMULATION

[75] Inventors: Andrew Sapsford; Andrew Patrick Savage, both of Ware, United Kingdom

[73] Assignee: Glaxo Group Limited, Greenford, United Kingdom

[21] Appl. No.: 08/849,217

[22] PCT Filed: Dec. 8, 1995

[86] PCT No.: PCT/EP95/04824

§ 371 Date: Jul. 21, 1997

§ 102(e) Date: Jul. 21, 1997

[87] PCT Pub. No.: WO96/18384

PCT Pub. Date: Jun. 20, 1996

[30] Foreign Application Priority Data

Dec. 10, 1994 [GB] United Kingdom .................. 9425160

[51] Int. Cl.$^7$ ...................................................... A61K 9/12
[52] U.S. Cl. ............................ 424/45; 424/46; 514/957; 514/958
[58] Field of Search ........................ 424/45, 46; 514/957, 514/958

[56] References Cited

U.S. PATENT DOCUMENTS 5,314,926  5/1994  Robin et al. .............................. 521/98
5,376,359  12/1994  Johnson ..................................... 424/45

FOREIGN PATENT DOCUMENTS

| 91 14422 | 10/1991 | WIPO . |
| 93 02150 | 2/1993 | WIPO . |
| 93 11743 | 6/1993 | WIPO . |
| 93 11745 | 6/1993 | WIPO . |
| 93 18746 | 9/1993 | WIPO . |
| 94 03153 | 2/1994 | WIPO . |

*Primary Examiner*—Thurman K. Page
*Assistant Examiner*—Lakshmi Channavajjala
*Attorney, Agent, or Firm*—Bacon & Thomas

[57] ABSTRACT

This invention relates to aerosol formulations of use in the administration of medicaments by inhalation. In particular, the formulations comprise (a) 1,1,1,2-tetrafluoroethane or 1,1,1,2,3,3,3-heptafluoro-n-propane or mixtures thereof as propellant, (b) 1,1,2,2,3-pentafluoropropane as co-propellant, and (c) particulate medicament. A method of treating respiratory disorders which comprises administration by inhalation of an effective amount of the pharmaceutical aerosol formulation is also described, as well as is a canister which is suitable for delivering the pharmaceutical aerosol formulation.

24 Claims, No Drawings

PROPELLANT MIXTURE FOR AEROSOL FORMULATION

This invention relates to aerosol formulations of use in the administration of medicaments by inhalation.

The use of aerosols to administer medicaments has been known for several decades. Such aerosols generally comprise the medicament, one or more chlorofluorocarbon propellants and either a surfactant or a solvent, such as ethanol.

The most commonly used aerosol propellants for medicaments have been $CCl_3F$ (propellant 11) in admixture with $CCl_2F_2$ (propellant 12) and $CF_2Cl.CF_2Cl$ (propellant 114). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise hydrogen-containing chlorofluorocarbons and fluorocarbons and a number of medicinal aerosol formulations using such propellant systems have been disclosed in, for example, EP 0372777, WP91/04011, WO91/11173, WO91/11495, WO91/14422, WO92/00061, WO92/00062 and WO92/00107.

These applications are all concerned with the preparation of pressurised aerosols for the administration of medicaments and seek to overcome the problems associated with the use of the new class of propellants, in particular the problems of stability associated with the pharmaceutical formulations prepared. These applications all propose the addition of a wide range of adjuvants such as alcohols, alkanes, dimethyl ether, surfactants (including fluorinated and non-fluorinated surfactants, carboxylic acids, polyethoxylates etc) and even conventional chlorofluorocarbon propellants in small amounts to minimise potential ozone damage.

Surprisingly, we have now found that mixtures of a non ozone-depleting propellant and a specific fluorinated hydrocarbon may be employed as propellant systems suitable for use in pharmaceutical aerosol compositions.

There is thus provided in one aspect of the invention an aerosol formulation comprising:

(a) 1,1,1,2-tetrafluoroethane ($CF_3CH_2F$), 1,1,1,2,3,3,3-heptafluoro-n-propane ($CF_3CHFCF_3$) or mixtures thereof as propellant;

(b) 1,1,2,2,3-pentafluoropropane as co-propellant; and (c) particulate medicament.

Generally, the ratio of propellant: co-propellant is in the range of about 30:70 to about 95:5, preferably 50:50 to 90:10 by weight, especially 50:50 to 80:20, for example 75:25 (w/w).

Medicaments which may be administered in aerosol formulations according to the invention include any drugs useful in inhalation therapy which may be presented in a form which is substantially completely insoluble in the selected propellant system. Appropriate medicaments may thus be selected from, for example, analgesics, e.g. codeine, dihydromorphine, ergotamine, fentanyl or morphine; anginal preparations, e.g. dilitiazem; antiallergics, e.g. cromolyn, cromogylcate or nedocromil; antibiotics, e.g. cephalosporins, penicillins, streptomycin, sulphonamides or tetracyclines; antihistamines, e.g. methapyrilene; anti-inflammatories, e.g. beclomethasone, flunisolide, fluticasone, tipredane, budesonide, triamcinolone acetonide; antitussives, e.g. noscapine; bronchodilators, e.g. ephedrine, epinephrine, fenoterol, formoterol, isoprenaline, isoproterenol, metaproterenol, phenylephrine, phenylpropanolamine, pirbuterol, repoterol, rimiterol, salbutamol, salmeterol, terbutaline or (−)-4-amino-3,5-dichloro-α-[[[6-[2-(2-pyridinyl) ethoxy]hexyl]amino] methyl]benzenemethanol; diuretics, e.g. amiloride, anticholinergics e.g. ipratropium bromide; hormones, e.g. cortisone, hydrocortisone or prednisolone; and therapeutic proteins and peptides, e.g. glucagon or insulin. It will be clear to a person skilled in the art that, where appropriate, the medicaments will be used in the form of salts (e.g. as alkali metal or amine salts or as acid addition salts) or as esters (e.g. lower alkyl esters) or as solvates (eg hydrates) to optimise the activity and/or stability of the medicament and/or to minimise the solubility of the medicament in the propellant.

Particularly preferred medicaments for administration using aerosol formulations in accordance with the invention include bronchodilators and anti-inflammatory steroids of use in the treatment of asthma by inhalation therapy, for example salbutamol (e.g. as the sulphate), salmeterol (e.g. as the hydroxynaphthoate known as salmeterol xinafoate), beclomethasone dipropionate or a solvate thereof, fluticasone propionate or (−)-4-amino-3,5-dichloro-α-[[[6-[2-(2pyridinyl) ethoxy]hexyl]amino]methyl] benzenemethanol.

The particle size of the particulate medicament should be such as to permit inhalation of substantially all of the medicament into the lungs upon administration of the aerosol formulation and will thus desirably be less than 20 microns, preferably in the range 1 to 10 microns, e.g. 1 to 5 microns. The particle size of the medicament may be reduced by conventional means, for example by milling or micronisation.

The final aerosol formulation desirably contains 0.005–10% w/w preferably 0.005–5% w/w, especially 0.01–1.0% w/w, of medicament relative to the total weight of the formulation.

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$. As used herein "substantially free" means less than 1% w/w based upon the propellant system, in particular less than 0.5%, for example 0.1% or less.

The propellant may optionally contain an adjuvant having a higher polarity and/or a higher boiling point than the propellant. Polar adjuvants which may be used include (e.g. $C_{2-6}$) aliphatic alcohols and polyols such as ethanol, isopropanol and propylene glycol, preferably ethanol. In general only small quantities of polar adjuvants (e.g. 0.05–3.0% w/w) may be required to improve the stability of the dispersion—the use of quantities in excess of 5% w/w may tend to dissolve the medicament. Formulations in accordance with the invention may preferably contain less than 1% w/w, e.g. about 0.1% w/w, of polar adjuvant. However, the formulations of the invention are preferably substantially free of polar adjuvants, especially ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example 1 to 30% w/w of a volatile saturated $C_{1-6}$ hydrocarbon.

Optionally, the aerosol formulations according to the invention may further comprise one or more surfactants. The surfactants must be physiologically acceptable upon administration by inhalation. Within this category are included surfactants such as oleic acid, sorbitan trioleate (Span$^R$ 85), sorbitan monooleate, sorbitan monolaurate, polyoxyetylene

(20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil and sunflower seed oil. Preferred surfactants are lecithin, oleic add and sorbitan trioleate.

An alternative class of surfactants are described in EP 0478686, especially surfactants of formula (I)

(I)

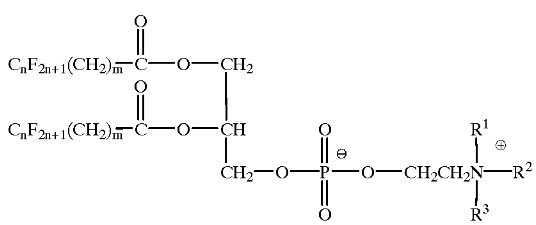

wherein n is an integer of 1 to 18, especially 2 to 12; m is an integer of 0 to 17, especially 0 to 11; and $R^1$, $R^2$ and $R^3$ are each independently a hydrogen atom or a $C_{1-4}$alkyl group.

Particularly preferred surfactants of formula (I) are the fluorinated phosphatidylcholines wherein RO1, $R^2$ and $R^3$ each represent methyl, n is an integer of 4 to 8, especially 4 or 6, and m is an integer of 4 to 10, especially 4 or 6.

If desired, the surfactant may be incorporated into the aerosol formulation in the form of a surface coating on the particulate medicament In this case, the use of substantially non-ionic surfactants which have reasonable solubility in substantially non-polar solvents is frequently advantageous since it facilitates coating of the medicament particles using solutions of surfactant in non-polar solvents in which the medicament has limited or minimal solubility.

The amount of surfactant employed in coating the particulate medicament is desirably in the range 0.1 to 10% w/w, preferably 1 to 10% w/w relative to the medicament. Where the surfactant is present as a surface coating, the amount may advantageously be chosen such that a substantially monomolecular coating of surfactant is formed. However, it is preferable that the formulations of the invention are substantially free of surfactants, i.e. contain less than an effective stabilising amount of a surfactant such as less than 0.0001% by weight of medicament.

The formulations of the invention may be prepared by dispersal of the medicament in the selected propellant and/or co-propellant in an appropriate container, e.g. with the aid of sonication. Preferably the particulate medicament is suspended in co-propellant and filled into, a suitable container. The valve of the container is then sealed into place and the propellant introduced by pressure filling through the valve in the conventional manner. Surprisingly, the aerosol formulations according to the invention have been found to be easily redispersed by mild agitation to provide suspensions with excellent delivery characteristics suitable for use in pressurised inhalers, even after prolonged storage.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The formulations according to the invention may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer coated and/or plastic-coated, which container is dosed with a metering valve. The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK356) and 3M-Neotechnic Ltd, UK (e.g. Spraymiser™).

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method the particulate medicament is first suspended in the co-propellant. The drug suspension is then filled into the empty canisters, valves crimped on and then propellant is pressure filled into the canisters through the valves in conventional manner. Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1,2,3 or 4 puffs each time.

The following non-imitative Examples serve to illustrate the invention.

Example 1

Micronised salmeterol xinafoate (hydroxynaphthoate, 8.7mg) was weighed into a clean, dry glass bottle together with 1,1,2,2,3-pentafluoropropane (1.3 g, 1 ml). The bottle was sealed by crimping a valve in place. Propellant 1,1,1, 2-tetrafluoroethane (20.7 g, 17 ml) was added, under pressure, through the valve. The resultant inhaler delivers 25 µg of salmeterol xinafoate (hydroxynaphthoate) per actuation (200 75 mg actuations per bottle). The ratio of propellant ($CF_3CH_2F$) to co-propellant ($CHF_2CF_2CH_2F$) was 17:1 (v/v).

Example 2

Micronised salmeterol xinafoate (hydroxynaphthoate, 8.7 mg) was weighed into a clean, dry glass bottle together with 1,1,2,2,3-pentafluoropropane (5.2 g, 4 ml). The bottle was sealed by crimping a valve in place. Propellant 1,1,1,2-tetrafluoroethane (17.1 g, 14 ml) was added, under pressure, through the valve. The resultant inhaler delivers 25 µg of salmeterol xinafoate (hydroxynaphthoate) per actuation (200 75 mg actuations per bottle). The ratio of propellant ($CF_3CH_2F$) to co-propellant ($CHF_2CF_2CH_2F$) was 14:4 (v/v).

Example 3

Micronised salmeterol xinafoate (hydroxynaphthoate, 4 mg) was weighed into a clean, dry aluminium aerosol canister (8 ml) together with co-propellant 1,1,2,2,3-pentafluoropropane (2 g). The canister was sealed by crimping a valve in place and propellant 1,1,1,2-tetrafluoroethane (10 g) was added, under pressure, through the valve. The resultant inhaler delivers 25 µg of salmeterol hydroxynaphthoate per actuation (120 75 mg actuations per can).

Examples 4 to 7

Inhalers were prepared as described in Example 3 containing propellant ($CF_3CH_2F$) to co-propellant ($CHF_2CF_2CH_2F$) in the ratios of 9:3, 8:4, 7;5 and 6:6 (w/w) (Examples 4, 5, 6 and 7 respectively).

Example 8

Micronised salbutamol (base) (24 mg) is homogenised with the aid of sonication in a solution of oleic acid (2.4 mg) in the co-propellant 1,1,2,2,3-pentafluoropropane (4.7 g) and filled into a dean, dry aluminium aerosol canister. The canister is sealed by crimping a valve in place. Propellant 1,1,1,2-tetrafluoroethane (14.1 g) is added, under pressure, through the valve The resultant inhaler delivers 100 microgram salbutamol per 75 mg actuation. The ratio of propellant ($CF_3CH_2F$) to co-propellant ($CHF_2CF_2CH_2F$) was 75:25 (w/w).

Examples 9 to 11

Inhalers are prepared as described in Example 8 containing propellant ($CF_3CH_2F$) and co-propellant ($CHF_2CF_2CH_2F$) in the ratios 70:30, 50;50 and 95:5 (w/w) (Examples 9, 10 and 11 respectively).

Example 12

Micronised salbutamol (base) (24 mg) is homogenised with the aid of sonication in a solution of oleic acid (2.4 mg) in the co-propellant 1,1,2,2,3-pentafluoropropane (5.3 g) and filled into a clean, dry aluminium aerosol canister. The canister is sealed by crimping a valve in place. Propellant 1,1,1,2,3,3,3-heptafluoro-n-propane (15.9 g) is added, under pressure, through the valve. The resultant inhaler delivers 100 microgram salbutamol per 75 mg actuation. The ratio of propellant ($CF_3CHFCF_3$) to co-propellant ($CHF_2CF_2CH_2F$) was 75:25 (w/w).

Examples 13 to 15

Inhalers are prepared as described in Example 12 containing propellant ($CF_3CHFCF_3$) to co-propellant ($CHF_2CF_2CH_2F$) in the ratios 70:30, 50:50 and 95:5 (w/w) (Examples 13, 14 and 15 respectively).

Example 16

Micronised fluticasone propionate (4 mg) is weighed into a clean, dry aluminium aerosol canister (8 ml) together with co-propellant 1,1,2,2,3-pentafluoropropane (3.1 g). The canister is sealed by crimping a valve in place. Propellant 1,1,1,2-tetrafluoroethane (9.3 g) is added, under pressure, through the valve. The resultant inhaler delivers 25 µg of fluticasone propionate per actuation (120 75 mg actuations per can). The ratio of propellant ($CF_3CH_2F$) to co-propellant ($CHF_2CF_2CH_2F$) is 9:3 w/w.

Example 17

Micronised salmeterol xinafoate (hydroxynaphthoate, 4 mg) and micronised fluticasone propionate (8 mg) are weighed into a clean, dry aluminium aerosol canister (8 ml) together with co-propellant 1,1,2,2,3pentafluoropropane (3.1 g). The canister is sealed by crimping a valve in place. Propellant 1,1,1,2-tetrafluoroethane (9.3 g) is added, under pressure, through the valve. The 10 resultant inhaler delivers 25 µg salmeterol xinafoate (hydroxynaphthoate) and 50µg fluticasone propionate per actuation (120 75 mg actuations per can). The ratio of propellant ($CF_3CH_2F$) to co-propellant ($CHF_2CF_2CH_2F$) is 9:3 w/w.

What is claimed is:

1. A pharmaceutical aerosol formulation comprising (a) 1,1,1,2-tetrafluoroethane, 1,1,1,2,3,3,3,-heptafluoro-n-propane or a mixture thereof as propellant; (b) 1,1,2,2,3-pentafluoropropane as a co-propellant; and (c) a particulate medicament selected from the group consisting of an analgesic; an anginal preparation; an anti-allergic; an antibiotic; an antihistamine; an antitussive; a bronchodilator, a diuretic, an anticholinergic; a hormone; and an anti-inflammatory agent selected from the group consisting of flunisolide, fluticasone, tipredane, budesonide, triaminolone acetonide and a salt, ester and solvate thereof.

2. A formulation according to claim 1 wherein the ratio of propellant:co-propellant is about 30:70 to about 95:5 by weight.

3. A formulation according to claim 2 wherein the ratio of propellant:co-propellant is about 50:50 to about 80:20 by weight.

4. A formulation according to claim 1 wherein the propellant comprises 1,1,1,2-tetrafluoroethane.

5. A formulation according to claim 1 wherein the propellant comprises 1,1,1,2,3,3,3-heptafluoro-n-propane.

6. A formulation according to claim 1 wherein the medicament is an anti-allergic, a bronchodilator or an anti-inflammatory steroid.

7. A formulation according to claim 1 wherein the medicament is salmeterol xinafoate.

8. A formulation according to claim 1 wherein the medicament is salbutamol sulphate.

9. A formulation according to claim 1 wherein the medicament is fluticasone propionate.

10. A formulation according to claim 1 wherein the medicament is formoterol, cromoglycate, terbutaline, reproterol or (−)-4-amino-3,5-dichloro-α-[[[6-[2-(2-pyridinyl)

ethoxy]hexyl]amino]methyl]benzemethanol budesonide, triamcinolone acetonide or a physiologically acceptable salt or solvate thereof.

11. A formulation according to claim 1 wherein the medicament is present in an amount of 0.005 to 10% w/w relative to the total weight of the formulation.

12. A formulation according to claim 11 wherein the medicament is present in an amount of 0.01 to 1% w/w relative to the total weight of the formulation.

13. A formulation according to claim 1 which contains two or more particulate medicaments.

14. A formulation according to claim 13 which contains salbutamol or salmeterol or a physiologically acceptable salt thereof in combination with an anti-inflammatory steroid or an anti-allergic.

15. A formulation according to claim 14 which contains salmeterol or salbutamol or a physiologically acceptable salt thereof in combination with fluticasone propionate or a physiologically acceptable solvate thereof.

16. A formulation according to claim 1 comprising an adjuvant having a higher polarity and/or a boiling point than the propellant.

17. A formulation according to claim 16 wherein the adjuvant having a higher polarity than the propellant is present in an amount of 0.05 to 5% w/w based upon the propellant and co-propellant.

18. A formulation according to claim 1 comprising a surfactant.

19. A canister suitable for delivering a pharmaceutical aerosol formulation which comprises a container capable of withstanding the vapour pressure of a propellant used, which container is closed with a metering value and contains a pharmaceutical aerosol formulation comprising (a) 1,1,1,2-tetrafluoroethane, 1,1,1,2,3,3,3,-heptafluoro-n-propane or a mixture thereof as propellant; (b) 1,1,2,2,3-pentafluoropropane as a co-propellant; and (c) a particulate medicament selected from the group an analgesic; an anginal preparation; an anti-allergic; an antibiotic; an antihistamine; an antitussive; a bronchodilator, a diuretic, an anticholinergic; a hormone; an anti-inflammatory agent selected from the group consisting of flunisolide, fluticasone, tipredane, budesonide, triaminolone acetonide, and a salt, ester and solvate thereof.

20. A canister according to claim 19 wherein the container is a metal can.

21. A canister according to claim 20 wherein the container is an aluminium can.

22. A canister according to claim 20 wherein the container is plastics-coated.

23. A metered dose inhaler which comprises a canister according to claim 19 fitted into a suitable channelling device.

24. A method of treating respiratory disorders which comprises administration by inhalation of an effective amount of a pharmaceutical aerosol formulation according to claim 1.

* * * * *